(12) United States Patent
Kaiser et al.

(10) Patent No.: US 7,331,982 B1
(45) Date of Patent: Feb. 19, 2008

(54) SUTURE ANCHOR AND ASSOCIATED METHOD

(75) Inventors: Ryan A Kaiser, Leesburg, IN (US); Kevin T Stone, Winona Lake, IN (US)

(73) Assignee: Biomet Sports Medicine, Inc., Warsaw, IN (US)

( * ) Notice: Subject to any disclaimer, the term of this patent is extended or adjusted under 35 U.S.C. 154(b) by 764 days.

(21) Appl. No.: 10/657,373

(22) Filed: Sep. 8, 2003

(51) Int. Cl.
*A61B 17/04* (2006.01)
(52) U.S. Cl. .................................................. 606/232
(58) Field of Classification Search ................ 606/232, 606/73, 60, 75, 104
See application file for complete search history.

(56) References Cited

U.S. PATENT DOCUMENTS

| | | | |
|---|---|---|---|
| 5,203,787 A | 4/1993 | Noblitt et al. | |
| 5,549,607 A | 8/1996 | Olson et al. | |
| 5,618,314 A | 4/1997 | Harwin et al. | |
| 5,810,821 A | 9/1998 | Vandewalle | |
| 5,833,463 A | 11/1998 | Hurson | |
| 5,851,219 A | 12/1998 | Goble et al. | |
| 5,961,528 A | 10/1999 | Birk et al. | |
| 5,980,558 A | 11/1999 | Wiley | |
| 6,022,352 A | 2/2000 | Vandewalle | |
| 6,045,573 A * | 4/2000 | Wenstrom et al. | 606/232 |
| 6,168,598 B1 | 1/2001 | Martello | |
| 6,264,677 B1 * | 7/2001 | Simon et al. | 606/232 |
| 6,379,362 B1 | 4/2002 | Birk et al. | |
| 6,471,707 B1 | 10/2002 | Miller et al. | |
| 6,537,274 B1 | 3/2003 | Katz | |
| 2002/0052629 A1 | 5/2002 | Margan et al. | |
| 2002/0147463 A1 | 10/2002 | Martinek | |
| 2002/0161401 A1 | 10/2002 | Steiner | |
| 2002/0173822 A1 | 11/2002 | Justin et al. | |
| 2003/0065361 A1 | 4/2003 | Dreyfuss | |
| 2003/0069604 A1 | 4/2003 | Schmieding et al. | |

OTHER PUBLICATIONS

Tiodize Process; Introduction to Tiodize and to the Tiodize Process; Tiodize/Michigan, Inc., Wixom, MI; pp. 1-28; 1995.

* cited by examiner

*Primary Examiner*—Kevin T. Truong
(74) *Attorney, Agent, or Firm*—Harness, Dickey & Pierce, P.L.C.

(57) ABSTRACT

Suture anchor and associated method and system. In one embodiment, the suture anchor includes a bone anchoring portion, and a suture securing portion coupled to the bone anchoring portion. The suture securing portion has an eyelet through which a suture is threaded. The eyelet has a surface finish provided by a coating process, such as a titanium nitride or a titanium anodize process that increases the life of the suture.

27 Claims, 1 Drawing Sheet

SUTURE ANCHOR AND ASSOCIATED METHOD

FIELD OF THE INVENTION

The present invention relates to a suture anchor having an eyelet, and associated method.

BACKGROUND OF THE INVENTION

It is often necessary to secure soft tissues, tendons and ligaments to bone during orthopedic surgical procedures in both human and animal patients. In the past, various devices and methods have been developed to accomplish this soft tissue attachment. In one known procedure, the orthopedic surgeon would make large incisions into the soft tissue to expose the bone, drill angled holes through the bone, and then thread the sutures through the holes in order to achieve ligament or soft tissue attachment. This known procedure was extremely complex and time consuming.

Due to the difficulties and potential complications associated with the previous procedures, alternate devices and methods have been developed. One such device for attaching soft tissues to a bone, developed to overcome some of the disadvantages of the previous devices and procedures, is the suture anchor. A suture anchor generally comprises an anchor member which can be seated within the bone. A suture strand is secured to the anchor member and, thus, is available for assisting in the attachment of soft tissues, tendons and ligaments to the bone. Suture anchors generally require less complex and time consuming surgical procedures than those associated with earlier methods for attaching soft tissue to bone.

However, there are improvements which can be made to existing known suture anchors to increase the life of the sutures and facilitate suture manipulation.

SUMMARY OF THE INVENTION

One embodiment of the invention provides a suture anchor including a bone anchoring portion, and a suture securing portion coupled to the bone anchoring portion. The suture securing portion has an eyelet through which a suture is threaded. The eyelet has a surface finish provided by a coating process that increases the life of the suture.

Another embodiment of the invention provides a surface treatment method for a suture anchor. The method includes providing a bone anchoring portion coupled to a suture securing portion, and forming a suture eyelet in the suture securing portion. The method also includes treating the eyelet with a coating process that provides a surface finish which increases the life of a suture threaded through the eyelet.

Yet another embodiment of the invention provides a suture anchoring system. The suture anchoring system includes a suture anchor and a suture. The suture anchor includes a bone anchoring portion, and a suture securing portion coupled to the bone anchoring portion. The suture securing portion has an eyelet through which the suture is threaded. The suture anchoring system also includes an eyelet surface finish, which is provided by a coating process. The surface finish increases the life of the suture.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF PRESENT EMBODIMENTS

The following description of present embodiments is merely exemplary in nature and is in no way intended to limit the invention, its application, or uses.

Figure 1:
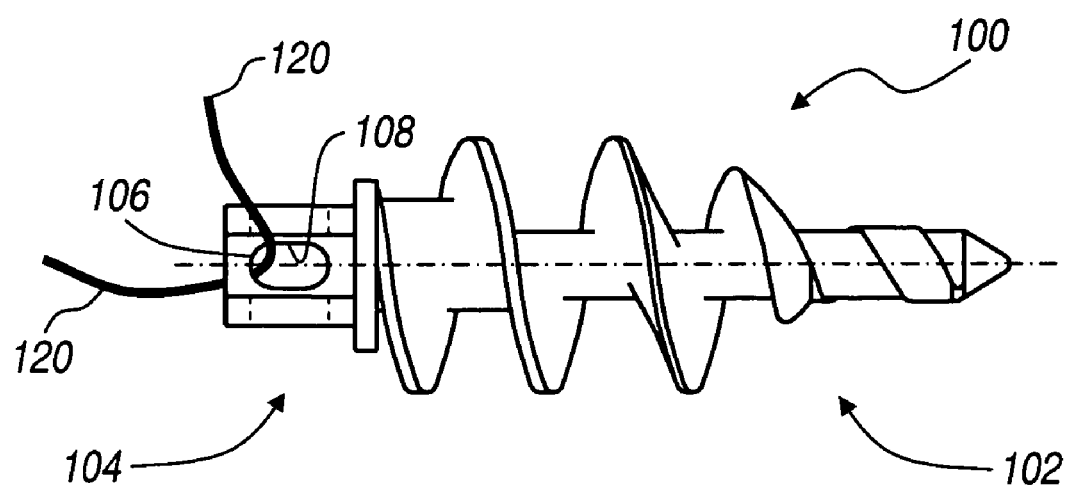
FIG. 1 is a perspective view of an embodiment of a suture anchor according to the invention.

An exemplary embodiment of a suture anchor 100 is shown in FIG. 1. The suture anchor 100 includes a bone anchoring portion 102 and a suture securing portion 104. The bone anchoring portion 102 and the suture securing portion 104 are coupled such that the suture anchor 100 can be integral or modular or articulated, for example. The bone anchoring portion 102 and the suture securing portion 104 may be made from the same or different materials. For example, the entire suture anchor may be made of titanium or a titanium alloy, or the suture securing portion 104 can be made of titanium or a titanium alloy, while the bone anchoring portion 102 can be made of any other biocompatible material, such as another metal or alloy, or a resorbable polymeric material such as, for example, Lactosorb®. The bone anchoring portion 102 may also include anchoring formations 130, such as threads, ridges, grooves, barbs, spikes, etc.

The suture securing portion 104 includes an eyelet 106, such as a bore or a hole or other opening, through which a suture 120 can be threaded through. While the eyelet 106 is illustrated as a through hole that passes perpendicularly to the longitudinal axis of the suture anchor 100, the eyelet 106 can take on any shape or size at any location relative to the suture anchor 100 to accommodate the suture 120. The eyelet 106 includes a surface finish 108 which is selected to reduce the wear of the suture 120 and increase its fatigue life. The surface finish 108 is such that it increases the lubricity of the eyelet 106 and reduces fretting wear damage of the suture 120, without changing any dimensions of the eyelet 106. Furthermore, the increased lubricity facilitates manipulating the suture 120, such as threading the suture 120 through the eyelet 120 or tying an arthroscopic knot or folding the suture 120 over the eyelet 106, etc. The surface finish 108 can be provided by a titanium nitride process, a titanium anodize process type II process or other process with similar properties. Prior art surface processes applied to eyelets such as blasting, tumbling and machining do not provide the above-described properties for eyelets 106.

The titanium anodize process that results in the surface finish 108 of the described properties in one embodiment of the suture anchor 100 is different from conventional anodizing. In conventional anodizing of a part, acid solutions or other chemicals are used, causing reduction or change of dimensions with a concomitant reduction in fatigue strength of the part Furthermore, acid treatment may deteriorate the surface quality of the part, promote galling and fretting, thereby exacerbating wear of any materials that are in frictional contact with the conventionally anodized surface.

Figure 2:
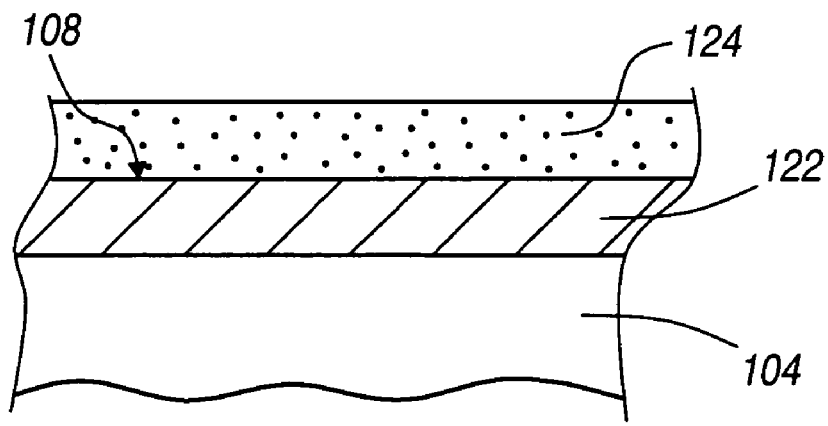
FIG. 2 is a schematic diagram of a surface finish provided by a titanium anodize process.

In contrast, the titanium anodize process that produces the surface finish 108 in one embodiment of the invention, is based on electrolysis using an alkaline bath. Referring to FIG. 2, the titanium anodize process typically produces a penetration layer 122, typically 0.0001 to 0.0003 inches, and a soft build-up layer 124 in the range of 0.001 to 0.003 inches. In the titanium anodize process type II, the build-up layer 124 is removed by processes known in the art, such as ultrasonic cleaning, burnishing with stainless steel wool, glass beading, etc. The resulting surface finish 108 does not change the dimensions of the eyelet 106.

The surface finish 108 of the eyelet 106 was subjected to several tests using a variety of sutures 120. In one test, for example, the surface finish 108 was provided by a titanium anodize process type II and was tested with a polyester #2 suture 120 subjected to a cyclic load of 2.2 lb at 1 Hz frequency with stroke of one inch. The life of the suture 120 was determined to be 498 cycles. Under the same conditions, but tested against a matte finish of a conventional titanium anchor eyelet, the life of the suture was 278 cycles. In this test, therefore, the surface finish 108 of the eyelet 106 increased the life of the suture by about 79%.

It will be appreciated that the surface finish 108 can be applied to the eyelet 106 of any type of suture anchor 100 that has a titanium securing portion 104, such as, for example, the anchors disclosed in U.S. Pat. No. 5,980,558, and U.S. Pat. No. 5,203,787, which are incorporated herein by reference. Furthermore, the surface finish may be applied to the entire suture securing portion 104 and/or to the bone anchoring portion 102.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A suture anchor comprising:
   a bone anchoring portion; and
   a suture securing portion coupled to the bone anchoring portion, the suture securing portion having an eyelet through which a suture is threaded, wherein the eyelet has a titanium anodize surface finish, the surface finish including a penetration layer produced by a titanium anodize process and exposed after a removable build-up layer is removed, and such that there is no dimensional change of the eyelet after the surface finish is applied.

2. The suture anchor of claim 1, wherein the surface finish increases the life if the suture and reduces wear.

3. The suture anchor of claim 2, wherein the bone anchoring portion has a titanium anodize surface finish including a penetration layer produced by a titanium anodize process and exposed after a removable build-up layer is removed, such that there is no dimensional change of the bone anchoring portion after the surface finish is applied.

4. The suture anchor of claim 1, wherein the surface finish increases lubricity of the eyelet.

5. The suture anchor of claim 1, wherein the surface finish increases fatigue strength of the eyelet.

6. The suture anchor of claim 1, wherein the bone anchoring portion includes anchoring formations.

7. The suture anchor of claim 6, wherein the anchoring formations are selected from the group consisting of barbs, ridges, threads, grooves and spikes.

8. The suture anchor of claim 1, wherein the bone anchoring portion is integral with the suture securing portion.

9. The suture anchor of claim 1, wherein the bone anchoring portion and the suture securing portion are separate portions.

10. The suture anchor of claim 1, wherein the suture anchoring portion has a titanium anodize surface finish.

11. A method of surface treatment for a suture anchor, the method comprising:
    providing a bone anchoring portion coupled to a suture securing portion;
    forming a suture eyelet in the suture securing portion for passing a suture;
    treating the eyelet with a titanium anodize process;
    creating a penetration layer on the eyelet;
    creating a soft build-up layer above the penetration layer;
    removing the build-up layer; and
    exposing the penetration layer defining an eyelet surface finish.

12. The method of claim 11, wherein the surface finish increases the life of the suture threaded through the eyelet.

13. The method of claim 11, wherein the surface finish reduces wear of the suture.

14. The method of claim 11, wherein the surface finish increases lubricity of the eyelet.

15. The method of claim 11, wherein the surface finish does not result in a dimensional change of the eyelet.

16. The method of claim 11, wherein the surface finish increases fatigue strength of the eyelet.

17. The method of claim 11, wherein the bone anchoring portion is integral with the suture securing portion.

18. The method of claim 11, wherein the bone anchoring portion includes anchoring formations.

19. The method of claim 11, further comprising treating the suture securing portion with a titanium anodize process.

20. The method of claim 11, further comprising treating the bone anchoring portion with a titanium anodize process.

21. A suture anchoring system comprising:
    a suture anchor including a bone anchoring portion and a suture securing portion coupled to the bone anchoring portion, the suture securing portion having an eyelet;
    a suture threaded through the eyelet; and
    an eyelet titanium anodize surface finish, the surface finish including a penetration layer produced by a titanium anodize process and exposed after a removable build-up layer is removed, and such that there is no dimensional change of the eyelet after the surface finish is applied that increases the life of the suture.

22. The suture anchoring system of claim 21, wherein the bone anchoring portion is integral with the suture securing portion.

23. The suture anchoring system of claim 21, wherein the bone anchoring portion includes anchoring formations.

24. The suture anchoring system of claim 21, wherein the surface finish does not result in a dimensional change of the eyelet.

25. The suture anchoring system of claim 21, wherein the suture securing portion has a titanium anodize surface finish.

26. The suture anchoring system of claim 21, wherein the bone anchoring portion has a titanium anodize surface finish.

27. The suture anchoring system of claim 21, wherein the suture anchor has a titanium anodize surface finish.

* * * * *

UNITED STATES PATENT AND TRADEMARK OFFICE
CERTIFICATE OF CORRECTION

PATENT NO. : 7,331,982 B1
APPLICATION NO. : 10/657373
DATED : February 19, 2008
INVENTOR(S) : Ryan A. Kaiser et al.

Page 1 of 1

It is certified that error appears in the above-identified patent and that said Letters Patent is hereby corrected as shown below:

Column 2
Line 53, "eyelet 120" should be --eyelet 106--.

Column 2
Line 66, "part" should be --part.--.

Signed and Sealed this

Ninth Day of September, 2008

JON W. DUDAS
*Director of the United States Patent and Trademark Office*